(12) United States Patent
Hinding

(10) Patent No.: US 11,954,906 B2
(45) Date of Patent: Apr. 9, 2024

(54) ENDOSCOPIC DEVICE, METHOD FOR VERIFYING AN IDENTITY OF A COMPONENT OF AN ENDOSCOPIC DEVICE, AND COMPUTER PROGRAM PRODUCT

(71) Applicant: KARL STORZ SE & Co. KG, Tuttlingen (DE)

(72) Inventor: Thomas Hinding, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 0 days.

(21) Appl. No.: 17/511,793

(22) Filed: Oct. 27, 2021

(65) Prior Publication Data

US 2022/0180096 A1 Jun. 9, 2022

(30) Foreign Application Priority Data

Dec. 7, 2020 (DE) ...................... 10 2020 132 454.5

(51) Int. Cl.
*G06V 20/00* (2022.01)
*G02B 23/24* (2006.01)
(Continued)

(52) U.S. Cl.
CPC ......... *G06V 20/00* (2022.01); *G02B 23/2438* (2013.01); *G02B 23/2469* (2013.01);
(Continued)

(58) Field of Classification Search
CPC .. H04N 23/69; G02B 23/2428; G02B 3/2484; A61B 1/00059
See application file for complete search history.

(56) References Cited

U.S. PATENT DOCUMENTS 6,537,207 B1 3/2003 Rice et al.
7,794,396 B2 * 9/2010 Gattani .................. H04N 23/69
600/173
(Continued)

FOREIGN PATENT DOCUMENTS

DE 20213926 U1 10/2002
DE 102006054148 B4 7/2009
(Continued)

OTHER PUBLICATIONS

European Search Report for corresponding European Patent Application No. 21205458.9, dated Apr. 19, 2022.

*Primary Examiner* — Rowina J Cattungal
(74) *Attorney, Agent, or Firm* — Jason H. Vick; Sheridan Ross, PC

(57) ABSTRACT

The invention relates to an endoscopic device, in particular medical or industrial endoscopic device, wherein the endoscopic device comprises, as components, a light source, an optical fiber, a camera, and an endoscope comprising an optical element or a plurality of optical elements, and at least one optical element comprises an optical marking for verifying an identity of the optical element and/or of the endoscope such that the optical marking can be detected by the camera for verifying the identity and/or a configuration of the endoscopic device. The invention furthermore relates to a method for verifying an identity of a component of an endoscopic device, and a computer program product for evaluating an image acquisition of an optical marking of an optical element and for identifying an endoscope of an endoscopic device.

23 Claims, 3 Drawing Sheets

(51) Int. Cl.
*G06K 7/12* (2006.01)
*G06K 7/14* (2006.01)
*H04N 23/69* (2023.01)
*A61B 1/00* (2006.01)
*A61B 1/04* (2006.01)
*A61B 1/07* (2006.01)
*H04N 23/50* (2023.01)

(52) U.S. Cl.
CPC ........... *G02B 23/2484* (2013.01); *G06K 7/12* (2013.01); *G06K 7/1417* (2013.01); *H04N 23/69* (2023.01); *A61B 1/00059* (2013.01); *A61B 1/04* (2013.01); *A61B 1/07* (2013.01); *H04N 23/555* (2023.01)

(56) References Cited

U.S. PATENT DOCUMENTS

| | | | |
|---|---|---|---|
| 2005/0159646 A1 | 7/2005 | Nordstrom et al. | |
| 2008/0262654 A1 | 10/2008 | Omori et al. | |
| 2010/0040355 A1* | 2/2010 | Craen | A61B 1/0019 396/90 |
| 2013/0046299 A1 | 2/2013 | Newkirk | |
| 2013/0176395 A1* | 7/2013 | Kazakevich | H04N 13/20 348/45 |
| 2016/0000306 A1* | 1/2016 | Takayama | A61B 1/00126 600/109 |
| 2016/0015247 A1 | 1/2016 | Irion et al. | |
| 2017/0112565 A1 | 4/2017 | Hirschfeld | |
| 2017/0172701 A1 | 6/2017 | Kube et al. | |
| 2020/0187766 A1* | 6/2020 | Zalevsky | A61B 1/07 |
| 2020/0337525 A1* | 10/2020 | Steiner | A61B 1/00055 |

FOREIGN PATENT DOCUMENTS

| | | | | |
|---|---|---|---|---|
| DE | 102013101158 A1 | | 8/2014 | |
| DE | 102013002832 A1 | | 9/2014 | |
| DE | 102014109888 A1 | | 1/2016 | |
| DE | 102014217095 A1 | | 3/2016 | |
| DE | 102015016233 A1 | | 6/2017 | |
| DE | 102016214990 A1 | * | 2/2018 | ........ G01M 11/0221 |
| DE | 102016214990 A1 | | 2/2018 | |
| DE | 102017103804 A1 | | 8/2018 | |
| EP | 2390645 B1 | | 5/2013 | |
| EP | 2641552 A2 | | 9/2013 | |

* cited by examiner

ENDOSCOPIC DEVICE, METHOD FOR VERIFYING AN IDENTITY OF A COMPONENT OF AN ENDOSCOPIC DEVICE, AND COMPUTER PROGRAM PRODUCT

CROSS-REFERENCE TO RELATED APPLICATIONS

This application claims the benefit under 35 U.S.C. 119(a) to German Patent Application No. 10 2020 132 454.5, filed 7 Dec. 2020, the disclosure of which is incorporated herein by reference in its entirety.

FIELD

The invention relates to an endoscopic device, in particular a medical or industrial endoscopic device, wherein the endoscopic device comprises, as components, a light source, an optical fiber, a camera and an endoscope having an optical element or a plurality of optical elements. Furthermore, the invention relates to a method for verifying an identity of a component of an endoscopic device, and a computer program product for evaluating an image acquisition of an optical marking of an optical element and for identifying an endoscope of an endoscopic device.

BACKGROUND

In medical and non-medical applications, endoscopes having a long shank are used, in order to introduce this into an inner cavity of a human or animal body, or into another object for an examination, such as into a pipeline. In addition to the endoscope itself, the endoscopic device comprises further components for uses of this kind, such as a light source, an optical fiber for connecting the light source to the endoscope, and a camera. Often, the components from different production runs and/or for different applications by one manufacturer, or even a plurality of manufacturers, are mechanically compatible with one another. Furthermore, adapters are freely available in commers which allow for mechanical coupling of the components of endoscopic devices by the same manufacturer or by different manufacturers.

As a result, a use of the endoscopic device involving a sub-optimally assembled combination of the components thereof, and/or a combination of said components that is not intended for the particular use, can easily occur. This can lead to serious problems during use; for example, if too large an optical fiber is used in too small an endoscope, too much heat arises at the coupling point. In addition, some combinations function only inadequately in principle, for example a laparoscope with an optical fiber of 2 mm diameter. An inappropriately assembled device can have significant consequences for a patient and can lead to an incorrect diagnosis if, for example, a fluorescence dye is used within the context of photodynamic diagnostics (PDD) or near infrared fluorescence is utilized when using indocyanine green (ICG), and on account of non-optimal combinations of the components the corresponding color signals cannot be optimally received, displayed, and/or identified.

In principle, incompatibility protection could be incorporated in a design of new devices comprising an endoscope and a camera, in order to prevent connection to earlier and/or different apparatuses and instruments. However, it is not possible to perform this in a manner that is economical and practical for the user or for the manufacturer of the endoscopic apparatus. Furthermore, it may be the case that the type of the endoscope originally used has to be changed during an endoscopic intervention, because the intervention has to be extended to other organs for example. Consequently, for practical reasons the components of an endoscopic device must also be exchangeable, as long as this results in a combination which is suitable for the relevant use.

Furthermore, in clinical procedures a plurality of medical instruments is handled and used. As a result, in the preparation and follow-up phase of a surgical operation, the required instruments must be provided, verified, and subsequently supplied to disposal or conditioning (sterilization). For this purpose, the medical instruments are typically provided with an outer marking, such as a one-dimensional code (barcode), or a two-dimensional code (matrix code), which can be read in using an associated optical reader. Furthermore, RFID (Radio Frequency Identification) transponders or RFID tags are known for identifying surgical instruments, wherein it is necessary in this case too for the identification to be read out using a corresponding external reader.

A robot comprising at least one movable arm element is known from DE 10 2013 002 832 A1, in the case of which robot the surgical instrument comprises an RFID chip or a barcode for optical identification, for the purpose of automatic instrument identification of the type of instrument fastened to the robot.

DE 10 2014 109 888 A1 describes a method and a device for verifying the light and/or image transmission properties of an endoscopic or exoscopic system, wherein the identification data of an identifier of the endoscope or exoscope and/or of the light carrier are read out externally in a contactless manner by means of RFID technology, or optically, for example by means of a barcode and barcode reader.

DE 10 2015 016 233 A1 proposes an annular RFID transponder for marking an endoscope, which is arranged for example in an eyecup of the endoscope.

EP 2 390 645 B1 describes a device for testing an endoscope, wherein the endoscope is arranged on a test card carrier so as to be movable relative to and in front of a test card, wherein the endoscope comprises identification elements such as a barcode, and the device for testing corresponding read elements, such as a barcode scanner, for reading the identification elements.

DE 10 2013 101 158 A1 relates to a medical device for forming a medical system composed of one or more medical apparatuses and corresponding coupling points, in which a one-dimensional or two-dimensional barcode are detected at an end of a data line, an optical fiber cable, an electrical wire or a discharge tube, by means of a barcode scanner, a camera comprising an image data processing means, or an RFID reader.

In EP 2 641 552 A2, a surgical instrument comprises an instrument body which can be operationally coupled to various types of end effector assemblies to be communicated, and a modular end effector arrangement comprises a removable control module which controls the power supply to the end effector assembly on the basis of the respective type of the end effector arrangement. For the coupling, different shafts and/or end effectors can comprise a respective color code, in order to distinguish between different lengths and/or types.

A disadvantage of identification codes applied to the outside of components of a multi-part medical or industrial device is that said codes either have to be manually verified by the user, which is error-prone, or additional optical, electronic and/or wireless appliances are required for reading in and/or identifying the outer code. Furthermore, in the case of codes applied to the outside there is the risk of said codes fading and/or becoming illegible over time due to repeated preparation and/or sterilization of the components.

US 2013/0046299 A1 describes an intelligent electrode device for monitoring the use of an electrosurgical electrode, wherein the electrosurgical electrode and a tracking element are arranged inside a cladding of the intelligent electrode system. The tracking element comprises a microchip for storing process data of the electrode. A disadvantage is that identification of the electrode takes place only during use, by comparing the processed process data with those of a serial number of known electrodes.

Furthermore, optical image acquisition and identification systems, for example using a camera, are known.

In DE 10 2014 217 095 A1, a connectable electrode comprises an optically detectable outer identification feature at the distal end of a surgical instrument, wherein an image of the outer electrodes is detected by means of an image acquisition system for detecting an operating field, and the image data are transmitted to a data processing unit by means of which an association of the identification feature of the electrode with an electrode type and a provided operating parameter is performed in by means of a database.

DE 10 2006 054 148 B4 discloses a device for optical detection of interference and/or codes in an examination region on a flat optical boundary surface of a transparent body comprising an illumination means, an image acquisition means, and an image processing means for evaluation, wherein, in the case of codes, the recorded images are automatically analyzed and decoded by the image processing computer by means of a character recognition program. For example a CCD camera arranged externally outside of the optical axis of the device is used as an image acquisition means.

US 2008/0262654 A1 discloses a robot system comprising a robot and an actuator unit comprising a connectable and releasable work unit, wherein, in the connection region, the work unit comprises a two-dimensional image code comprising information relating to the work unit, and a camera for identifying the two-dimensional image code or for image acquisition, and LEDs for illumination, are arranged on the opposing contact surface of the actuator unit, such that an image of the two-dimensional image code can be recorded by means of the camera.

In DE 10 2017 103 804 A1, an imaging optics of an endoscopy camera is used for reading in an item of information which is aligned purposely for identifying an object to be examined endoscopically, for example a patient. For this purpose, the imaging optics of the endoscopy camera is directed for example to a code, to be read in, on a patient card. Subsequently, an item of identification information is extracted from the image of the code by means of corresponding programming of an associated image processing unit.

A disadvantage of all the known devices and methods for identification of a medical or industrial device is in particular the fact that the application of an identification code to the outside is not tamper-proof, and is subject to wear during use. Furthermore, there is a need for separate apparatuses for reading out the identification code, or separately arranged and/or oriented cameras for detecting a corresponding image of the identification code, in the case of identification codes of the known devices arranged both on the outside and on the inside.

The object of the invention is that of improving the prior art.

The object is achieved by an endoscopic device, in particular medical or industrial endoscopic device, wherein the endoscopic device comprises, as components, a light source, an optical fiber, a camera, and an endoscope comprising an optical element or a plurality of optical elements, and at least one optical element comprises an optical marking for verifying an identity of the optical element and/or of the endoscope such that the optical marking can be detected by the camera for verifying the identity and/or a configuration of the endoscopic device.

As a result, an endoscopic device is provided which, when the components are configured correctly, can be used for a particular medical or industrial examination, which advantageously verifies the identity of the optical element and/or of the endoscope even before this use. Thus, an automatic component and/or instrument identification is provided, for verifying and/or monitoring the identity of a component or a plurality of components, in particular of the endoscope, which has been configured for a particular medical or industrial intervention.

By detecting the optical marking as the identification code, the components of the endoscopic device that are required for a particular use and can be functionally interconnected are identified and verified, such that a medical intervention or an industrial examination can be carried out correctly and in an error-free manner. Consequently, serious problems, such as too great a development of heat at the coupling point of two components which are not compatible, or incorrect image acquisition in the case of a particular light and/or fluorescence dye mode, and consequently an incorrect diagnosis for a patient, can be prevented.

Specifically in cases in which the different components from different production ranges of a manufacturer or different manufacturers can be mechanically coupled to one another either directly or by means of commercially available adapters, detecting the optical marking of a component makes it possible to determine and/or verify the functionally correct connection and configuration of the endoscopic device, and/or the connection and configuration that is optimal for a particular use.

It is particularly advantageous that the optical marking is an inherent and/or permanent part of the component and/or of the endoscope, such that this is not subject to manipulation and/or susceptibility to errors.

For this purpose, the optical marking is preferably arranged on and/or in a fixed part of the component, such as an optical element of the endoscope.

In particular, it is advantageous for the imaging camera of the endoscopic device, which is used directly for image acquisition of the object field to be examined, to also directly detect the optical marking of the optical element beforehand. As a result, an additional camera, in particular an additional camera arranged externally, is not required. Furthermore, the camera of the endoscopic device does not have to be specially oriented and/or arranged for the detection of the optical marking, but rather the detection takes place in the arrangement and/or configuration already provided for the subsequent medical or industrial examination. Consequently, the camera inside the endoscopic device is already in the arrangement and/or orientation which is required for carrying out a particular medical or industrial intervention. Consequently, the endoscopic device is directly ready for use following positive verifying of the identity. Consequently, as well as a specially designed camera for the detection of an identification code, there is also no need for an external and/or additional reader for identifying the identification code in the endoscopic device. As a result, the installation size of the endoscopic device is smaller than that of known devices according to the prior art.

Furthermore, the detection using the in-built camera of the endoscopic device allows for quick identification of the identity of the component, and consequently a quick change from one endoscope type to another, if this may be necessary for example within one operation. This allows both for verifying of the identity of the endoscope directly after the first connection of the components prior to the planned intervention, and for monitoring and/or a change of the endoscope during the intervention. In principle, detection and/or identification of the endoscope in use in each case is made possible in every use situation of the endoscopic device.

Furthermore, it is advantageously also possible for a camera from an earlier production range to be used together with an endoscope comprising an optical element and an optical marking, in the endoscopic device. Likewise, it is possible to use an older endoscope in the endoscopic device, in that an existing optical element is exchanged for a new optical element comprising an optical marking, such that in any case an identity of the optical element and/or of the endoscope can be detected and identified. Consequently, simple retrofitting of already existing endoscopes is possible, in that for example only the eyepiece comprising a marking and an old eyepiece of the endoscope are exchanged.

One of the essential concepts of the invention is based on the fact that the endoscopic device, as a medical system, is already configured, with its components, for a particular medical intervention, and, in this configuration and/or arrangement, detects the optical marking of an optical element of a component and/or of the endoscope by means of its own camera for image acquisition of the object field within the endoscopic device, and is used for identification and/or verification of the medical system for carrying out the particular medical intervention.

The following terms should be explained:

An "endoscopic device" is in particular a medical or industrial system for endoscopic examination comprising a plurality of components. An endoscopic device in particular comprises at least one light source, an optical fiber, a camera, and an endoscope itself. The endoscopic device is assembled, oriented, and thus configured, for the respective use, from the components required therefor.

A "light source" is in particular a device from which light is emitted, which light is coupled into the endoscope. The light source is in particular arranged externally and connected to the endoscope by means of an optical fiber, wherein the optical fiber is in particular guided via a plug-in connection, further towards the distal end of a shaft of the endoscope. The light source in particular ensures homogeneous illumination of the examination. The light source is in particular an LED light source and/or a cold-light source. The light source can be designed as a stand-alone device, or can be directly integrated in a processor unit for image processing. Likewise, the light source can comprise an air/$CO_2$ insufflator and can be designed therewith as one device. In this case, the light source also comprises the insufflation pump. Likewise, the light source, insufflation pump, processor unit, and/or a monitor can be formed in a single device. The light source is in particular adjusted to the type and/or the optical properties of the camera.

An "optical fiber" (also referred to as a "fiber-optic cable") is in particular a cable and/or a wire which consists of optical fibers and is intended for transmitting light. An optical fiber can also be assembled by means of a plug-in connector. An optical fiber in particular comprises fibers made of quartz glass and/or plastics material, for guiding the light. An optical fiber can in particular also be a gel optical fiber or a fluid optical fiber, which conducts the light using a gel and/or a fluid as the transport medium. The optical fiber can also be integrated in a supply tube which supplies the endoscope with a medium or further media, such as a rinsing fluid.

A "camera" is in particular a phototechnical device for digital reproduction of the inspection. For this purpose, the camera is attached, in particular to the endoscope, by means of a camera head. In this case, the digital reproduction can take place using an external monitor or using a monitor that is directly integrated on and/or in the camera. The camera head can in particular be connected to the endoscope by means of an eyepiece. As a result, the camera in particular allows for an indirect visual verification of the test card and/or of the image of the object field. The camera head in particular has an HD resolution. The camera and/or the camera head can in particular also serve as a handle for the user.

An "endoscope" is in particular a device by means of which the inside of humans or animals or technical cavities can be examined and/or manipulated. An endoscope is in particular a rigid endoscope comprising a rigid shaft, or a flexible endoscope comprising a flexible shaft. An endoscope is in particular a video endoscope having digital image generation and transmission towards the proximal end of the video endoscope. At least one digital and/or electronic image sensor is arranged in particular at a distal end (remote from the user) of the long shaft of the endoscope. A video endoscope is any type of digital endoscope, for example a laparoscope or a gastroscope. In addition to applications in human and animal medicine, a video endoscope can, however, be used for industrial purposes, for example for a visual verification of cavities which are difficult to access. In industrial applications, an endoscope is frequently also referred to as a borescope.

An "optical element" is in particular an element for allowing passage of, for shaping, and/or for changing, a light beam. The optical element is in particular arranged in the beam path of the endoscope and/or along the optical axis. The optical axis is in particular an imaginary line which defines the path over which the light propagates through the endoscope and/or the objective lens system thereof, as far as the distal end and/or the electronic image sensor. The optical axis preferably extends through the center point of the optical element. The optical element in particular comprises glass and/or plastics material. An optical element can for example be a lens or an eyepiece.

An "optical marking" is in particular an applied, introduced and/or affixed marking, on and/or in an optical element. An optical marking is in particular an identification code which is detected and/or identified by means of the camera. As a result, the optical marking contains information relating to the identity of the optical element and/or of the endoscope. The optical marking is preferably applied to an optical element which is arranged in the interior of the endoscope, such that the optical marking cannot be removed and/or tampered with. However, the optical marking can also be arranged on the outside of the endoscope, for example on the inside of the eyecup, which is directed towards the camera.

In a further embodiment of the endoscopic device, two optical elements, three optical elements, and/or a plurality of optical elements each comprise one optical marking.

As a result, a plurality of components of the endoscope, which are for example connected so as to form the endoscope, such as the eyepiece and the portion comprising the shaft, are in each case optically marked and identified. Likewise, however, a single optical element can also be provided in a redundant manner with two or more optical markings. Likewise, a plurality of lenses of an objective system, arranged along the optical axis, can each comprise an optical marking, and thus ensure redundancy in the identification.

The second, third and/or more optical elements are preferably optical elements defined above, in the respective function and embodiment.

In order to adjust the detection and/or determination of the identity to the type of the endoscope, the components thereof, and/or the optical requirement, and the type of intended use, the optical element and/or the optical elements is/are an eyepiece, a lens, in particular a rod lens, and/or a cover glass.

As a result, the optical element which comprises the optical marking can be purposely selected from a plurality of possible optical elements from the proximal end, for example the eyepiece, to the distal end, the cover glass, of the endoscope. For example, the serial number can be located, as an optical marking, in plain text, as a barcode, or as a QR code, on the inner cover glass side, in the cover glass of the endoscope. It is particularly advantageous for one optical element or a plurality of optical elements, comprising respective optical markings, to be provided along the entire length dimension of the endoscope, which elements are arranged internally, rigidly connected and/or so as to be locally immovable, in the interior of the endoscope. As a result, the relevant optical marking is not subject to signs of wear and tear and attrition, for example due to the cleaning and disinfection, and nor is outside tampering with the optical marking possible.

An "eyepiece" is in particular an optically effective part of an optical system arranged on the eye side and/or camera side. An eyepiece in particular comprises a single lens or a lens system. An eyepiece is in particular a part of the endoscope by means of which it is possible to view the object field and/or the inspection point by eye. For the purpose of digital reproduction of the inspection, the endoscope can be connected via the eyepiece to the camera head of the camera.

A "lens" is in particular a transparent optical body which focusses or scatters a light beam or a plurality of light beams, by means of refraction. A lens is in particular a spherical or aspherical lens.

A "rod lens" is in particular a cylinder lens which is polished at the periphery and cut at both ends. A rod lens can in particular be used for optical fiber coupling.

A "cover glass" is in particular a planar, round glass, which closes the distal end of the tubular shaft. The cover glass is in particular connected to the distal end of the shaft in a fluid-tight and gas-tight manner, for example by means of adhesive bonding, plastics overmolding, or glazing.

In a further embodiment of the endoscopic device, the camera comprises a zoom lens having an adjustment means for changing a focal length, such that it is possible to detect the optical marking or the optical markings in a region from a proximal end to a distal end of the endoscope, in each case in a defined marking zoom position, using the zoom lens.

As a result, the camera focuses, by means of the zoom lens, to such an extent that it both detects and/or identifies optical markings applied in the cover glass or in the lens system, and also detects a serial number introduced into the eyepiece for example, at the opposing proximal end of the endoscope. Consequently, the camera can focus fully into the endoscope, from the proximal end thereof (close to the user) to the distal end (remote from the user). It is particularly advantageous for the camera to detect and make visible the relevant optical marking of an optical element in the respectively defined marking zoom positions, and thus focuses.

A "zoom lens" (also referred to for short as "zoom") is in particular a lens having a variable focal length. The adjustment means of the zoom lens brings about a change in the focal length, in particular by displacement of lens elements in the objective. For this purpose, the adjustment means can be actuated in particular manually, for example by rotating or shifting a ring on the lens, or in a motorized manner, by pressing zoom button.

A "defined marking zoom position" is in particular a defined setting of the zoom lens in which the optical marking is detectable and/or visible.

In order for the view of the object field and/or the image acquisition to be free of an optical marking, the zoom lens can be adjusted, using the adjustment means, such that, in an object zoom position for viewing an object to be examined, an image of the camera in the object zoom position is free of the optical marking or the optical markings.

As a result, during normal work and in the case of the intended use of the endoscope for carrying out a particular medical intervention or an industrial examination, the optical marking is not visible for the user, on the image acquisition and/or the monitor.

As a result, focusing on an optical marking, for example in the cover glass of the endoscope, can initially take place promptly, by means of the zoom lens and the adjustment means, in the defined marking zoom position, and directly thereafter, following identification of the cover glass, the focusing is continued in order to achieve a defined object zoom position, such that the optical marking is invisible, and the object to be examined is optimally visible. As a result, interference by the optical marking when observing the object to be examined is prevented.

Furthermore, focusing on a defined marking zoom position and a defined object zoom position makes it possible to switch very quickly and efficiently between a mode for determining the identity, and a conventional examination mode.

An "object zoom position" is in particular a zoom position of the zoom lens that is set using the adjustment means, in which position the object to be examined, and/or the recorded image of the camera, is free of an optical marking. As a result, the object field to be examined is optimally visible and/or fully illuminated in the object zoom position.

In a further embodiment of the endoscopic device, the optical marking and/or the optical markings is/are a line marking, a color marking, a QR code, a serial number, and/or plain text.

As a result, the most suitable optical marking in each case can be used for each optical element, wherein all the markings can in principle be detected by means of the camera.

As a result, the camera identifies for example a serial number in the optical lens system in the shaft of the endoscope, at a particular focus, as well as the serial number in the eyepiece of the endoscope.

Furthermore, a redundancy in the detection of the identity can also be provided, by means of different optical markings, for example a serial number, a QR code, and a barcode, on different optical elements of the endoscope.

A "line marking" is in particular an optoelectronically readable script which consists of parallel lines and/or gaps between the lines, which are of different widths or the same width. The line marking in particular represents the identity data in binary symbols. A line marking can in particular be a barcode. The identity data in the line marking are in particular read in by machine, using the camera as the optical reader, and electronically shared and/or further processed.

A "color marking" is in particular an optical marking which comprises a particular color or a plurality of colors. The color marking in particular comprises an identification color which can be associated with an identity. A color marking can also comprise a particular dye which is visible only in the case of irradiation with a particular light, such as UV or IR light.

A "QR code" is in particular an optical marking which comprises a two-dimensional code. The QR code consists in particular of a quadratic matrix made up of black and white quadrants which represent the coded identity data in a binary manner. In particular an orientation is specified in the QR code, in three of the four corners of the quadrant, by means of a special marking. The camera in particular generates a digital image of the QR-coded data and/or subsequently converts the coded identification data, contained in the image, into text form, and thus decodes said data.

A "serial number" is in particular a clear designation of a product by the manufacturer. The serial number in particular denotes the optical element, components of the endoscope, and/or the endoscope. The serial number is in particular also an identifier for the components and/or the endoscope of a series, and/or allows the production thereof to be traced.

For the purpose of optimal application and/or fixing of the optical marking depending on the material of the respective optical element and/or the optical properties of the endoscope, the optical marking is etched, engraved, lasered, printed and/or written into and/or onto the optical element or the optical elements.

In a further embodiment of the endoscopic device, the optical marking s arranged in the center, on the outer edge, and/or transversely over a surface of the optical element or the optical elements.

As a result, depending on the shape of the relevant optical element, and/or the arrangement thereof within the beam path and/or along the optical axis, an optimal position of the marking can be selected. Furthermore, as a result a distinction between the mode of the visible optical marking for identification, and the mode of the optimal visible object field for examination, can additionally be made.

In order for the optical marking to be visible only under certain light conditions, the optical marking can comprise a dye, in particular a UV and/or fluorescence dye.

It is thus possible, for example, for an optical marking comprising a fluorescence dye to be selected such that the emission wavelength of the fluorescence dye is not disruptive in the event of observation of the object field in the visible and/or white light range. Likewise, in the case of photodynamic diagnostics, the fluorescence emission of a fluorescence dye used diagnostically can be considered undisturbed if the optical marking is designed comprising a dye which neither absorbs nor emits light in this wavelength. As a result, purposeful selection of a dye for the marking also makes it possible for visibility and invisibility of the optical marking to be achieved by the respective light properties alone, independently of the defined marking zoom position and/or the defined object zoom position.

A "fluorescence dye" is in particular a dye which emits fluorescence light having a high wavelength, in the case of excitation of light having a short wavelength.

A "UV dye" (also referred to as "photochromatic dye") is in particular a dye which reacts to irradiation with UV light by way of a reversible shade change. In the case of a UV dye, the irradiated UV light in particular changes the chemical structure of the UV dye, and thus changes the absorption behavior thereof. For example, the UV dye changes from white to violet, blue, yellow, and/or red.

In a further embodiment, the endoscopic device is associated with an image and/or data processing means for evaluating and processing a recorded image and/or identifying the relevant optical marking of the relevant optical element and/or the optical elements, or the endoscopic device comprises the image and/or data processing means.

Following evaluation and processing of the recorded image data using the image and/or data processing means, and the clear identification of the relevant optical element and/or of the endoscope, the image and/or data processing means can enable and/or block the configuration of the endoscopic device for the planned medical intervention. For this purpose, a corresponding output is issued to the user, and/or a function of the endoscopic device is enabled or blocked. For example, in the case of an endoscope that is unsuitable for the PDD or ICG mode, coupling of light into said endoscope can be interrupted directly, via the image and/or data processing means.

Likewise, in the case of a delivered endoscopic device comprising a plurality of components, operation can be made possible only if the camera has detected the specified optical markings, and the image and/or data processing means has evaluated and correctly identified these.

The image and/or data processing means can furthermore comprise the camera control unit and/or the processor unit, already described above. Furthermore, the image and/or data processing means can also control all or just some functions of the endoscopic device. Of course, the image and/or data processing means can also be integrated directly in the camera. The image and/or data processing means in particular comprises software which directly identifies the optical marking and emits a response and/or notification to the user, such as displaying a warning, which is dependent on the identification result.

In an additional aspect of the invention, the object is achieved by a method for verifying an identity of a component of an endoscopic device, wherein the endoscopic device comprises, as components, a light source, an optical fiber, a camera, and an endoscope comprising an optical element or a plurality of optical elements, said method comprising the following steps of:

configuring the endoscopic device by arranging and/or connecting the light source, the optical fiber, the camera, and the endoscope comprising an optical element or a plurality of optical elements, focusing the camera on at least one optical marking of one of the optical elements, recording an image of the at least one optical marking by means of the camera, analyzing the recorded image and identifying the at least one optical marking and/or the optical element of the endoscope, repeating the focusing, recording, analyzing and identifying of a further optical marking of a further optical element, and/or outputting a result of the identification for a medical or industrial application of the configured endoscopic device.

As a result, a verification of an identity of a component of the endoscopic device, and thus the optimal configuration of said device for a particular intended use, is to be carried out directly before said use, by means of the method, without the endoscopic device having to be reconstructed and/or arranged differently for verifying the identity or for the subsequent examination of the object in the case of a positive result of the identification. Consequently, following successful identification, the planned medical intervention or the industrial application can be started directly, without loss of time.

In a further embodiment of the method, the optical marking or the optical markings is/are not visible when focusing the camera on an object to be examined.

In order to automatically carry out the method for verifying the identity of a component, following connection, and thus configuration, of the components of the endoscopic device, the focusing of the camera is performed automatically upon connection to the endoscope or upon activation of the endoscope.

Thus, the method is started automatically and does not have to be manually triggered by a user. For the automatic identification, when the endoscope is pushed onto the camera head, on account of the changed light conditions or a magnetic switch, the camera identifies than an endoscope has been pushed on. The camera subsequently automatically moves the zoom lens into the provided marking zoom position, in order to perform an identification for example of a serial number as the optical marking. In the event of a positive result of the identification, the corresponding functions of the endoscopic device, for the planned use, are subsequently enabled automatically.

In another aspect, the object is achieved by a computer program product for evaluating an image acquisition of an optical marking of an optical element and for identifying an endoscopic device described above, wherein the computer program product comprises commands which, upon execution of the computer program product by an image and/or data processing means, perform an identification of the optical marking in the image acquisition, an association of the identified optical marking with a particular optical element and/or with a particular endoscope, and thus an identification of the particular optical element and/or of the particular optical endoscope, and/or an output of a notification to the user of the endoscopic device.

BRIEF DESCRIPTION OF THE DRAWINGS

The invention will be described in more detail in the following with reference to embodiments in which.

DETAILED DESCRIPTION

Figure 1:
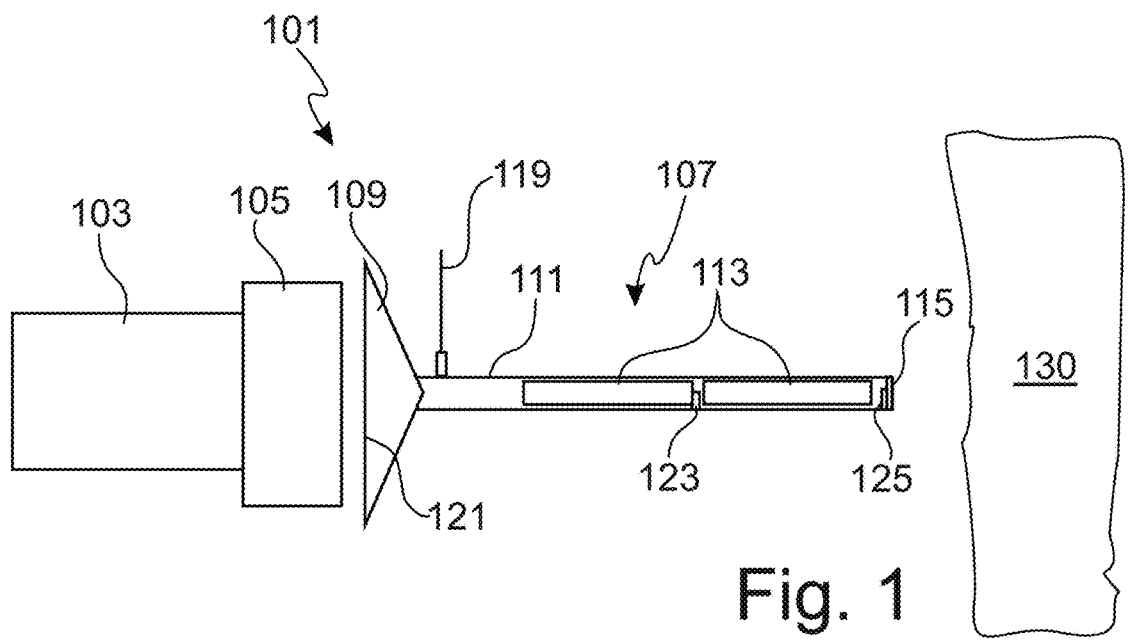
FIG. 1 is a highly schematic view of an endoscopic device comprising a camera and an endoscope directed to a tissue.
Figure 2:
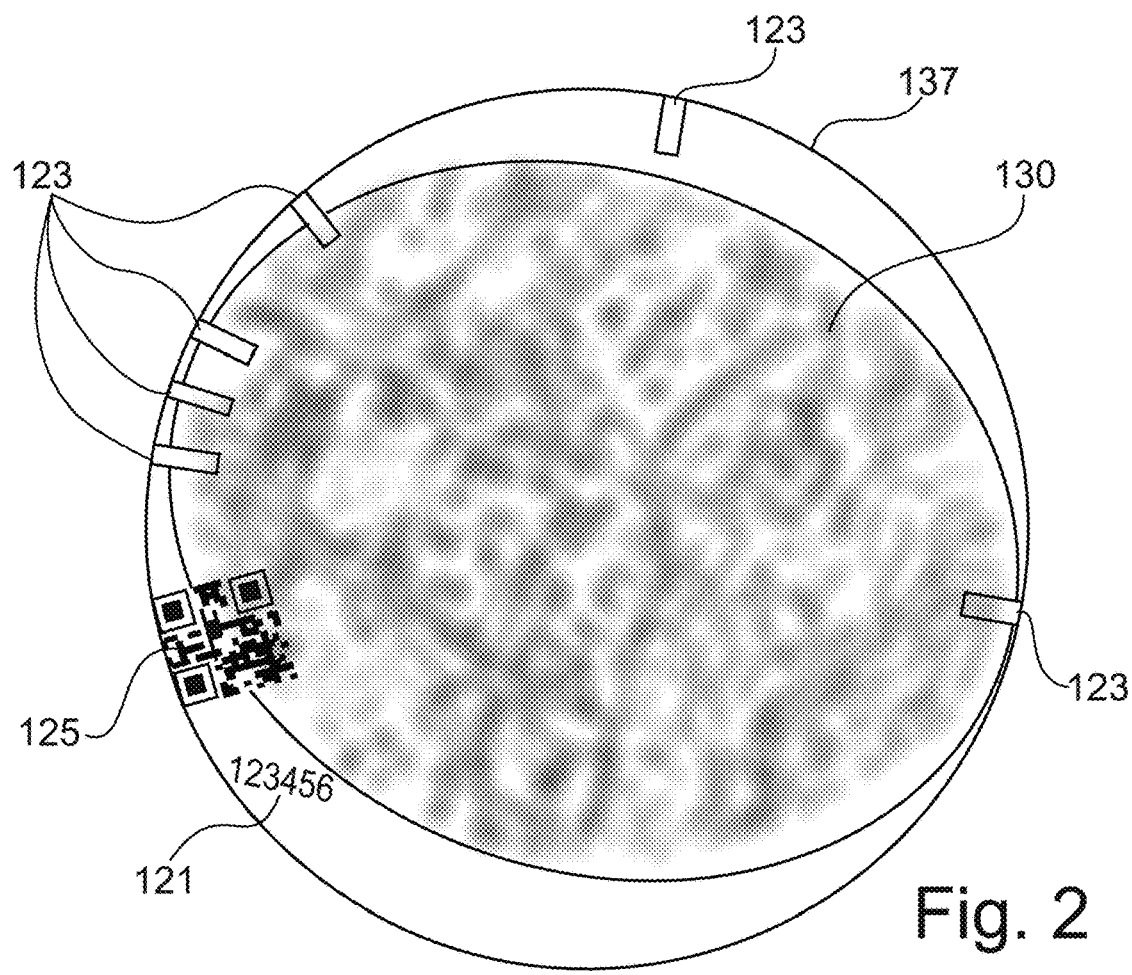
FIG. 2 shows an image acquisition of the camera when looking through the endoscope, having in each case a sharply focused barcode, QR code and serial number, and an unfocussed view of the tissue.
Figure 5:
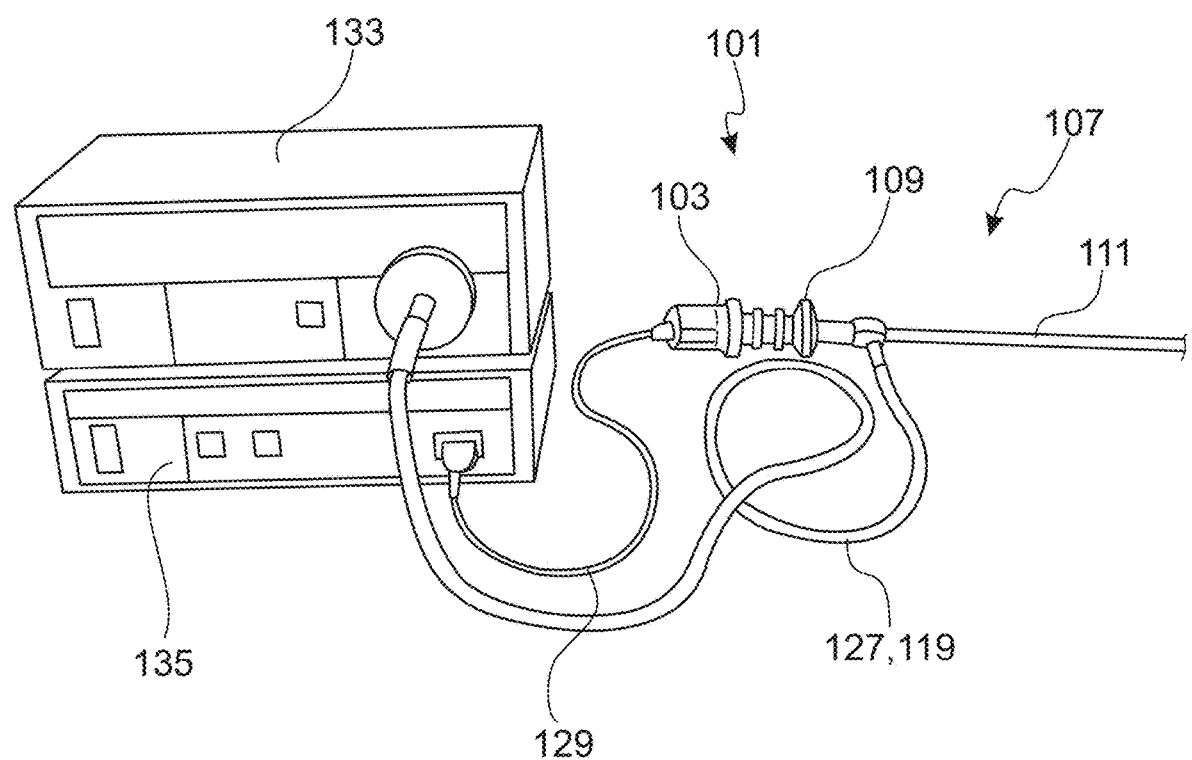
FIG. 5 is a three-dimensional view of the endoscopic device.

An endoscopic device 101 comprises a camera 103 having a camera zoom 105, a light source 133 adjusted to the camera 103, and an endoscope 107 (FIGS. 1 and 5). The camera 103 and the camera zoom 105 is followed, in the distal direction, by an eyepiece 109 of the endoscope 107. In addition to the eyepiece 109, the endoscope 107 comprises an elongate shaft 111.

Together with the endoscope 107, an optical fiber 119 is guided in a supply tube 127 by means of an optical fiber connection, and the camera 103 is connected to an image and data processing means 135 via a video cable 129 (FIG. 5). The optical fiber 119 is connected to the light source 133 for feeding light into the optical fiber 119. In the interior, inside the shaft 111, the endoscope 107 comprises two rod lenses 113. The shaft 111 is closed at the distal end by means of a cover glass 115. The eyepiece 109 comprises a serial number 121 as the identification code. Furthermore, in the distal direction, at the distal side thereof, the first rod lens 113 comprises a barcode 123, and the cover glass 115 comprises a QR code 125 at the proximal side thereof. The endoscopic device 101 is already fully configured for the planned use for examining a tissue 130 (FIG. 1).

Figure 3:
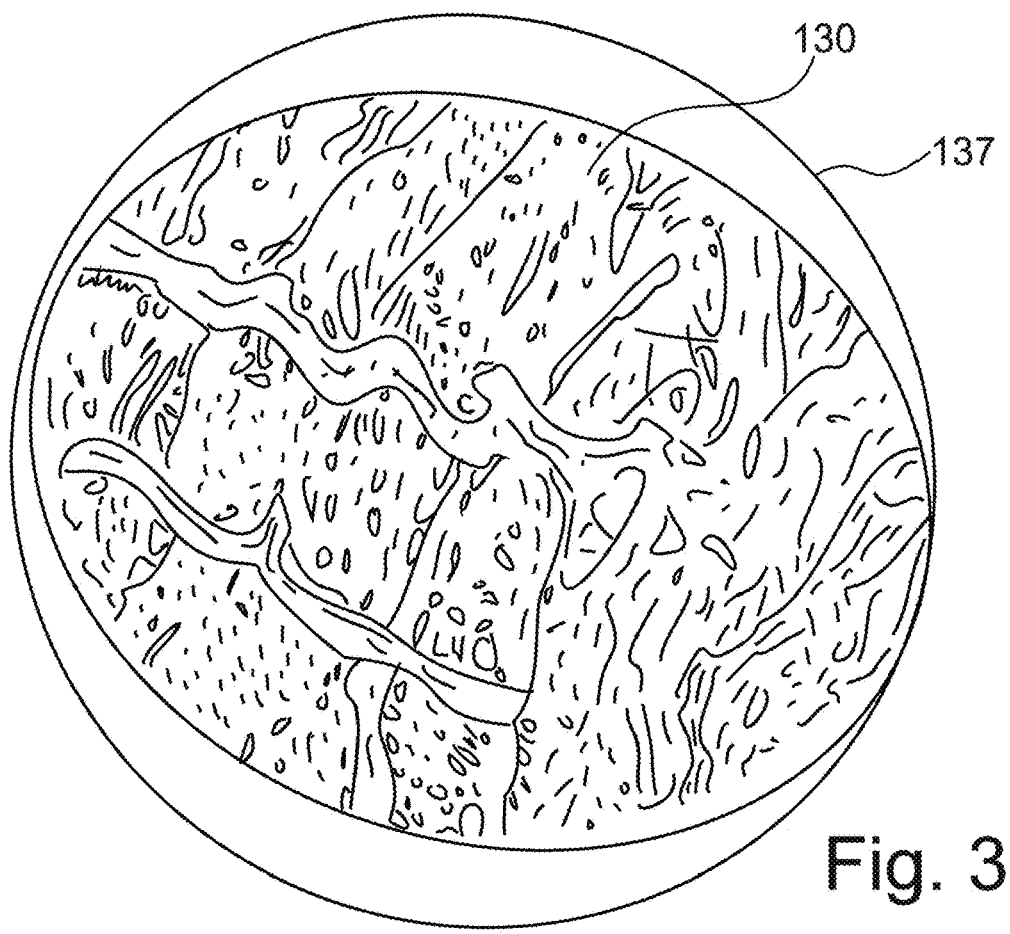
FIG. 3 shows an image acquisition of the camera when looking through the endoscope, having a focus on the visible tissue free of the codes from FIG. 2.
Figure 4:
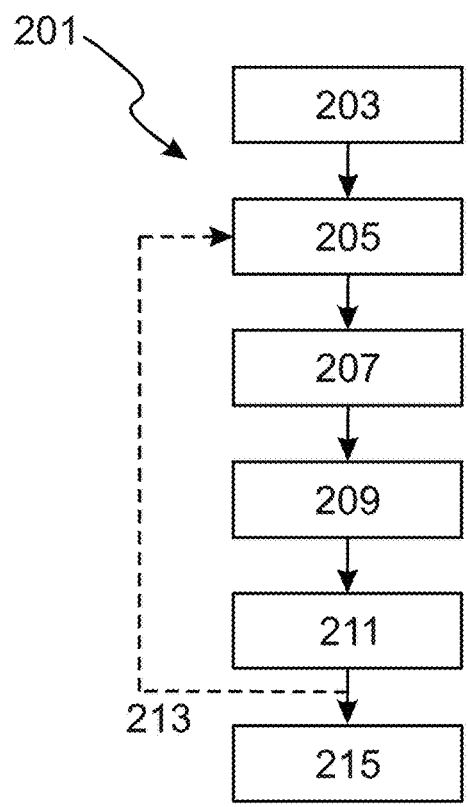
FIG. 4 shows the method for verifying the configuration/identity.

By means of the camera zoom 105 the camera is now focused on a first marking zoom position for detecting the serial number 121 of the eyepiece 109, the serial number 121 on the edge of the eyepiece 109 is detected, and the image data are evaluated, and the serial number 121 identified by means of the image and data processing means 135. Subsequently, the camera 103 focusses, by means of the camera zoom 105, on a second marking zoom position for detecting the barcode 123 at the distal side of the first rod lens 113. The correspondingly recorded image data as in the case of the serial number 121 are also evaluated and identified for the barcode 123. In the next step focusing on a third marking zoom position for detecting the QR code 125 on the proximal side of the cover glass 115 is carried out by means of the camera zoom 105. The evaluation and identification are performed in an equivalent manner for the QR code 125 (in this respect, it is noted that in FIG. 3 all three marking zoom positions, entered in succession, are shown together, with the corresponding image acquisition of the relevant code in the field of view 137, but are seen in succession by the user).

The identification of the serial number 121 of the eyepiece 109, the barcode 123 of the first rod lens 113, and the QR code 125 of the cover glass 115 reveals that the endoscope 107 is optimally suitable for the planned endoscopic intervention on the tissue 130, and is suitable for use together with the camera 103 and the light source 133. Thereupon, a user immediately begins the examination of the tissue 130, said user moving the distal end of the shaft 111 of the endoscope 107 towards the tissue 130. In this case, the tissue 130 is clearly visible for the user, without the serial number 121, the barcode 123, and the QR code 125 being visible in the image acquisition in the field of view 137 (see FIG. 3).

Consequently, a method for configuration/identity verifying 201 is provided, in which firstly a configuration 203 of the endoscopic device 101 for a planned, particular endoscopic use is carried out. Subsequently focusing 205 of the camera 103 by means of the camera zoom 105 is carried out, in the case of which, in a defined marking zoom position, an image acquisition 207 of an optical marking 121, 123 or 125 is performed using the camera 103. In the next step, the recorded image 209 is analyzed using an image and/or data processing means (step 209), and identification 211 of the optical marking takes place. In the case of further optical markings in the endoscopic device 101, there is a repetition 213 of steps 205 to 211, or the result of the identification 211 is output to the user (step 215). The output 215 to the user can take place in the form a warning signal, a display, and/or enabling or blocking of a function of the endoscopic device 101.

As a result, an endoscopic device 101 is provided in which the already configured endoscopic device 101 promptly directly verifies the identity of the endoscope 107, using the imaging camera 103, before the actually planned use, and, in the case of a positive identification, directly enables the endoscopic device 101 for the use that is now to be performed. Consequently, it is possible to identify the individual components of the endoscope 107, and thus the endoscope 107 itself, as well as to perform the specified examination of the tissue 130, using the same endoscopic device 101.

LIST OF REFERENCE CHARACTERS 101 endoscopic device
103 camera
105 camera zoom
107 endoscope
109 eyepiece
111 shaft
113 rod lens
115 cover glass
119 optical fiber
121 serial number
123 barcode
125 QR code
127 supply tube
129 video cable
130 tissue
133 light source
135 image and data processing means
137 field of view
201 method for verifying the configuration/identity
203 configuring
205 focusing the camera
207 image acquisition of an optical marking
209 analyzing the image
211 identifying
213 repeating using a further optical marking
215 output to the user

The invention claimed is:

1. An endoscopic device comprising:
a light source,
an optical fiber,
a camera, and
an endoscope having one or more optical elements, the camera being attached to the endoscope by a camera head, wherein at least one optical element of the one or more optical elements is a lens inside the endoscope and comprises an optical marking configured to allow verification of one or more of: an identity of the at least one optical element and of the endoscope, such that the each optical marking can be detected by the camera to verify one or more of: an identity, and a configuration of the endoscopic device, wherein:
the at least one optical element is arranged within a beam path, and
each optical marking is within the beam path.

2. The endoscopic device according to claim 1, wherein two or more optical elements each comprise a respective optical marking, the respective optical markings being within the beam path.

3. The endoscopic device according to claim 2, wherein another optical element of the one or more optical elements is a cover glass that comprises an optical marking.

4. The endoscopic device according to claim 1, wherein the at least one optical element is a portion of an eyepiece or a rod lens.

5. The endoscopic device according to claim 1, wherein the camera comprises a zoom lens having an adjustment mechanism configured to change a focal length to detect the optical marking or the optical markings in a region from a proximal end to a distal end of the endoscope, in each case in a defined marking zoom position, using the zoom lens.

6. The endoscopic device according to claim 5, wherein the zoom lens can be adjusted, using the adjustment mechanism, such that, in an object zoom position for viewing an object to be examined, an image of the camera in the object zoom position is free of the optical marking or the optical markings.

7. The endoscopic device according to claim 1, wherein the optical marking and/or the optical markings is or are one or more of: a line marking, a color marking, a QR code, a serial number, and plain text.

8. The endoscopic device according to claim 1, wherein the optical marking is one or more of: etched, engraved, lasered, printed, and written in and/or written on the optical element or the optical elements.

9. The endoscopic device according to claim 1, wherein the optical marking is arranged in one or more of: the center, on the outer edge, and transversely over a surface of the optical element or the optical elements.

10. The endoscopic device according to claim 1, wherein the optical marking comprises one or more of: a dye, a UV dye, and a fluorescence dye.

11. The endoscopic device according to claim 1, wherein the endoscopic device is associated with an image and/or data processing system, the image and/or data processing system configured to evaluate and process a recorded image and/or identify the relevant optical marking of the optical element and/or the optical elements, or the endoscopic device comprises the image and/or data processing system.

12. A method to verify an identity of a component of an endoscopic device, wherein the endoscopic device comprises a light source, an optical fiber, a camera and an endoscope comprising one or more optical elements, the method comprising:
configuring the endoscopic device by one or more of: arranging and connecting the light source, the optical fiber, the camera, via a camera head, and the endoscope,
focusing the camera on at least one optical marking of one of the optical elements, wherein the at least one optical element of the one or more optical elements is a lens arranged within a beam path inside the endoscope, the at least one optical marking within the beam path configured to allow verification of an identity of the one or more optical elements,
recording an image of the at least one optical marking by the camera,
analyzing the recorded image and identifying one or more of: the at least one optical marking and the at least one optical element of the endoscope, repeating the focusing, recording, analyzing and identifying of a further optical marking of a further optical element and/or outputting a result of the identification or identifications.

13. The method according to claim 12, wherein when focusing the camera on an object to be examined, the optical marking or optical markings is or are not visible.

14. The method according to claim 12, wherein the focusing of the camera is carried out automatically upon connection with the endoscope or upon activation of the endoscope.

15. An endoscopic device comprising:
a camera, and
an endoscope, the endoscope having one or more optical elements, the camera being attached to the endoscope by a camera head, wherein at least one optical element of the one or more optical elements is a lens within the endoscope, and comprises an optical marking configured to allow verification of an identity of: one or more of the optical element, and of the endoscope, wherein the optical marking is detectable by the camera to verify one or more of: an identity, and a configuration of the endoscopic device, wherein the at least one optical element:
is arranged within a beam path of the endoscope, and
each optical marking is within the beam path.

16. The endoscopic device according to claim 15, wherein two or more optical elements each comprise a respective optical marking, the respective optical markings being within the beam path.

17. The endoscopic device according to claim 16, wherein another optical element of the one or more optical elements is a cover glass that comprises an optical marking.

18. The endoscopic device according to claim 15, wherein the at least one optical element is an eyepiece, or a rod lens.

19. The endoscopic device according to claim 15, wherein the camera comprises a zoom lens having an adjustment mechanism configured to change a focal length to detect the optical marking or the optical markings in a region from a proximal end to a distal end of the endoscope.

20. The endoscopic device according to claim 19, wherein the zoom lens can be adjusted, using the adjustment mechanism, such that, in an object zoom position for viewing an object to be examined, an image of the camera in the object zoom position is free of the optical marking or the optical markings.

21. The endoscopic device according to claim 15, wherein the optical marking and/or the optical markings is or are one or more of: a line marking, a color marking, a QR code, a serial number, and plain text.

22. The endoscopic device according to claim 15, wherein the optical marking is one or more of: etched, engraved, lasered, printed, and written in and/or written on the optical element or the optical elements.

23. An endoscopic device comprising:
a light source,
an optical fiber,
a camera,
an endoscope having one or more optical elements, the camera being attached to the endoscope by a camera head, wherein at least one optical element of the one or more optical elements is a lens inside the endoscope, the at least one optical element includes an optical marking configured to allow verification of one or more of: an identity of one or more of the at least one optical element, and of the endoscope, such that each optical marking can be detected by the camera, and
instructions stored on a non-transitory computer-readable information storage media, the instructions, when executed by one or more processors, verify one or more of: an identity, and a configuration of the endoscopic device, wherein:
the at least one optical element is arranged within a beam path, and
each optical marking is within the beam path.

* * * * *